United States Patent
Yamada et al.

(10) Patent No.: US 10,191,017 B2
(45) Date of Patent: Jan. 29, 2019

(54) DYNAMIC CHARACTERISTIC CALCULATION APPARATUS AND ITS METHOD FOR MACHINE TOOL

(71) Applicant: JTEKT Corporation, Osaka-shi (JP)

(72) Inventors: Yoshihiko Yamada, Anjo (JP); Hiroshi Watanabe, Nagoya (JP); Takayuki Azuma, Anjo (JP); Kenji Hamada, Kariya (JP)

(73) Assignee: JTEKT CORPORATION, Osaka-shi (JP)

( * ) Notice: Subject to any disclaimer, the term of this patent is extended or adjusted under 35 U.S.C. 154(b) by 1044 days.

(21) Appl. No.: 13/926,356

(22) Filed: Jun. 25, 2013

(65) Prior Publication Data

US 2014/0012519 A1 Jan. 9, 2014

(30) Foreign Application Priority Data

Jul. 6, 2012 (JP) ................................. 2012-152337
Jul. 6, 2012 (JP) ................................. 2012-152340

(51) Int. Cl.
*G01N 29/44* (2006.01)
*G01N 29/12* (2006.01)
(Continued)

(52) U.S. Cl.
CPC ....... *G01N 29/4454* (2013.01); *B23Q 17/098* (2013.01); *B23Q 17/12* (2013.01); *G01N 29/045* (2013.01); *G01N 29/12* (2013.01)

(58) Field of Classification Search
CPC .. G01N 29/4454; G01N 29/045; G01N 29/12; B23Q 17/098; B23Q 17/12; B23Q 3/002
See application file for complete search history.

(56) References Cited

U.S. PATENT DOCUMENTS

2004/0093191 A1* 5/2004 Jeppsson ............... G01N 29/12
703/1
2004/0236529 A1* 11/2004 Esterling ............ B23Q 17/0976
702/108
(Continued)

FOREIGN PATENT DOCUMENTS

CN 1079716 C 2/2002
CN 1349877 A 5/2002
(Continued)

OTHER PUBLICATIONS

Wu and Siegel Correlation of Accelerometer and Microphone Data in the "Coin Tap Test", IEEE Transaction on Instrumentation and Measurement, 49(3) 2000, p. 493-497.*
(Continued)

*Primary Examiner* — Regis Betsch
*Assistant Examiner* — Catherine Rastovski
(74) *Attorney, Agent, or Firm* — Oblon, McClelland, Maier & Neustadt, L.L.P.

(57) ABSTRACT

A dynamic characteristic calculation apparatus for a machine tool calculates dynamic characteristic of the machine tool executing an interrupted machining by moving a rotational tool relative to a workpiece. The apparatus includes a detector detecting acoustic wave generated by vibration of the rotational tool or detecting magnetic property being variable by the vibration of the rotational tool where said rotational tool is excited to vibrate, and a calculation division calculating a natural frequency f of the one or plural tool tips in a vibration system, in which the one or plural tool tips of said rotational tool is a vibration body, on a basis of a value detected by the detector.

14 Claims, 8 Drawing Sheets

(51) Int. Cl.
*G01N 29/04* (2006.01)
*B23Q 17/09* (2006.01)
*B23Q 17/12* (2006.01)

(56) References Cited

U.S. PATENT DOCUMENTS

| | | | |
|---|---|---|---|
| 2007/0001638 A1* | 1/2007 | Gray | B25J 9/1692 |
| | | | 318/568.11 |
| 2009/0187270 A1* | 7/2009 | Hoefler | B23C 5/003 |
| | | | 700/177 |
| 2010/0305898 A1 | 12/2010 | Yamaguchi et al. | |
| 2011/0301929 A1* | 12/2011 | Huang | G06F 17/5018 |
| | | | 703/7 |
| 2012/0010744 A1* | 1/2012 | Yamashita | B23Q 15/12 |
| | | | 700/173 |

FOREIGN PATENT DOCUMENTS

| | | | |
|---|---|---|---|
| CN | 1352586 | * | 6/2002 |
| CN | 1352586 A | | 6/2002 |
| CN | 1903489 A | | 1/2007 |
| JP | 11-19850 | | 1/1999 |
| JP | 2003-340627 A | | 12/2003 |
| JP | 2004-249441 A | | 9/2004 |

OTHER PUBLICATIONS

Extended European Search Report dated Sep. 20, 2013, in European Patent Application No. 13174468.2.
Combined Chinese Office Action and Search Report dated Aug. 22, 2016 in Patent Application No. 201310282095.6 (English translation only).
Partial English translation of Office Action dated Apr. 19, 2016 in Japanese Patent Application No. 2012-152337.

* cited by examiner

DYNAMIC CHARACTERISTIC CALCULATION APPARATUS AND ITS METHOD FOR MACHINE TOOL

INCORPORATION BY REFERENCE

The present application claims priority under 35 U.S.C. § 119 to Japanese Patent Applications No. 2012-152337, filed on Jul. 6, 2012 and No. 2012-152340, filed on Jul. 6, 2012. The contents of these applications are incorporated herein by reference in the entirety.

BACKGROUND OF THE INVENTION

1. Field of the Invention

The present invention relates to a dynamic characteristic calculation apparatus and method thereof calculating a dynamic characteristic of a tool tip of a rotational tool in a vibration system, in which the tool tip of the rotational tool is a vibration body, in a machine tool executing a machining by the rotational tool of an end mill and so on.

2. Description of the Related Art

It is important for deciding a proper machining condition to identify dynamic characteristic of a machine tool in order to high precision machining by a rotational tool of an end mill and so on. In a prior art of US2010/0305898 A1, it is disclosed a dynamic rigidity calculation of a spindle by detecting an amount of run-out of an un-balance master that is equipped on the spindle. In another prior art of Japanese Laid-open Publication Tokkai-Hei 11-19850, it is disclosed a dynamic rigidity measurement of a spindle by measuring a displacement of measured target with means of exciting to vibrate the measured target of a spindle, a tool or a dummy tool mounted on the spindle etc. by magnetic attraction of a magnet. A displacement sensor is disclosed to be an eddy current displacement sensor, an inductance displacement sensor, an optical displacement sensor, a capacitance displacement sensor and so on.

On the other hand, since it tends to use a smaller rotational tool with a longer protruding amount of the rotational tool for higher accurate machining, an amount of deflection of the rotational tool becomes larger. Therefore, it is needed to measure dynamic characteristic in a vibration system including the rotational tool because it is not sufficient to measure the dynamic rigidity of the spindle itself as shown in the prior arts. It is hard to obtain the dynamic characteristic in a state that the dummy tool is mounted on the spindle in the prior art. The eddy current displacement sensor should be installed precisely, thereby increasing the installing time.

SUMMARY OF THE INVENTION

In view of the previously mentioned circumstances, it is an object of the present invention to provide a dynamic characteristic calculation apparatus of a machine tool and a method of calculation of the its dynamic characteristic to measure the dynamic characteristic in a vibration system including a rotational tool used for actual machining easily and precisely.

It is pointed out that an acoustic wave detector or a magnetic property detector can be used to detect a vibration status of a rotational tool even though the vibration of the rotational tool is small in its amount and short in its duration.

In order to achieve the above and other objects, one aspect of the present invention provides a dynamic characteristic calculation apparatus calculating dynamic characteristic of a machine tool to execute an interrupted machining by moving relative to a workpiece a rotational tool having one or plural tool tips comprising, a detector detecting acoustic wave generated by vibration of said rotational tool or detecting magnetic property being variable by said vibration of said rotational tool where said rotational tool is excited to vibrate, and a calculation division calculating a natural frequency of said one or plural tool tips in a vibration system, in which said one or plural tool tips of said rotational tool is a vibration body, on a basis of a value detected by said detector. By way of detecting the acoustic wave or the magnetic property, the present invention can achieve higher precision machining by deciding a machining condition on a basis of the natural frequency of the tool tips in deflection and vibration of the tool tips to the base portion by the interrupted machining. Since the detector can be positioned in relatively loose in comparison with a capacitance displacement sensor of the prior art needing accurate positioning, it may not need any skilled technology and it can reduce installing time.

The second aspect of the present invention provides mainly exciting means to vibrate said rotational tool by a hammer member by a human. Thereby, this method is easily performed without additional setting of equipments. The hitting amplitude and direction by the human does not affect largely to detecting accuracy so that the hitting operation is done without any human attention. Since the hitting operation is performed to excite the actual rotational tool itself, it generates the high accurate dynamic characteristic.

The third aspect of the present invention provides mainly exciting means to vibrate said rotational tool by contacting said rotational tool with a target member mounted on said machine tool by driving said driving device. Thereby, this makes possibility of automatic vibration of the rotational tool during the rotation for hammering without a man power. Since the automatic vibration is performed to hit the actual rotational tool, it is possible to produce high precision dynamic characteristic. Since the hit is done without the man power, it is performed just before a real machining, thereby presenting the dynamic characteristic just prior to the actual machining. Since an amount of the exciting power to vibrate the rotational tool is set precisely, it is possible to vibrate the rotational tool surely to be detected by the detector.

The fourth aspect of the present invention provides mainly exciting means to vibrate said rotational tool by contacting said rotational tool with said target member by driving said driving device during said rotational tool is rotated to a counter rotational direction against a rotational direction in machining. Thereby, since the rotational tool is rotated to a counter rotational direction against a rotational direction in machining, the target member contacted with the rotational tool can not be machined, therefore reducing wear of the target member.

The fifth aspect of the present invention provides mainly exciting means to vibrate said rotational tool by contacting a non-tip portion of said rotational tool with said target member by driving said driving device. Thereby, since the non-tip portion of said rotational tool is contacted with the target member, there is no damage to the tool tips, therefore increasing a life of the tool tips.

The sixth aspect of the present invention provides mainly exciting means to vibrate said rotational tool by contacting said non-tip portion of said rotational tool with said target member by driving said driving device during said rotational tool is rotated to same rotational direction to a rotational direction in machining. Thereby, since the vibration is performed to hit the actual rotational tool in rotating, it is possible to produce high precision dynamic characteristic similar to the actual dynamic characteristic of the rotational tool in machining.

The seventh aspect of the present invention provides mainly said dynamic characteristic of said one or plural tool tips including said natural frequency and a mass coefficient in said vibration system, and a FEM analysis division obtaining said mass coefficient by executing FEM analysis based on constructional information of said machine tool. The dynamic characteristic is easily obtained by the FEM analysis and the mass coefficient can be obtained easily by the FEM analysis division. An actual mounting position of the rotational tool on the tool holder becomes to be slightly different from a designed mounting position in detail by the FEM analysis division because of a possible displacement of positioning by the operator. Therefore, the FEM analysis by the FEM analysis division is not precisely same to the analysis of the actual position of the rotational tool mounted on the tool holder. On the other hand, since the acoustic wave or magnetic property detected by the detector is that generated by the actual vibration of the rotational tool, the acoustic wave or magnetic property is based on the actual position of the rotational tool on the tool holder. The natural frequency obtained by the FEM analysis division is different from the natural frequency calculated by the calculation division. Therefore, the natural frequency is calculated on a basis of the acoustic wave or the magnetic property as actual natural frequency without using the natural frequency obtained by the FEM analysis.

The eighth aspect of the present invention provides mainly said FEM analysis division obtaining said natural frequency by executing FEM analysis, and said detector detecting said acoustic wave or said magnetic property in detecting condition decided on a basis of said natural frequency obtained by said FEM analysis division. The detector includes a plurality of frequency bands and detects the acoustic wave with certain frequency band being set in a range of the frequency bands. The range of the frequency bands as a detecting condition of the detector is set as a range of the detected frequency bands including the natural frequency obtained by the FEM analysis division. Thereby, the detector can obtain the acoustic wave or the magnetic property including the actual natural frequency certainly and finely.

The ninth aspect of the present invention provides mainly said dynamic characteristic including damping ratio in said vibration system, and said calculation division calculating said damping ratio on a basis of said detected value by said detector. Since the damping ratio is different from the damping ratio obtained by the FEM analysis because of the installed position difference of the rotational tool. Therefore, the damping ratio is calculated based on the acoustic wave or the magnetic property detected by the detector to decide the machining condition with the detected one, thereby obtaining the desired machining accuracy.

The tenth aspect of the present invention provides mainly said dynamic characteristic of said one or plural tool tips including damping ratio in said vibration system, said FEM analysis division obtaining said damping ratio by executing FEM analysis. The damping ratio is easily obtained by FEM analysis. Deflection of damping ratio affects smaller damage to the machining accuracy than deflection of the natural frequency. Therefore, it obtains the damping ratio by the FEM analysis easily, thereby obtaining enough machining accuracy.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DETAILED DESCRIPTION OF THE PREFERRED EMBODIMENTS

It is hereinafter explained embodiments of a dynamic characteristic calculation apparatus for a machine tool according to the present invention.

"Machine Construction of the Machine Tool"

Figure 1:
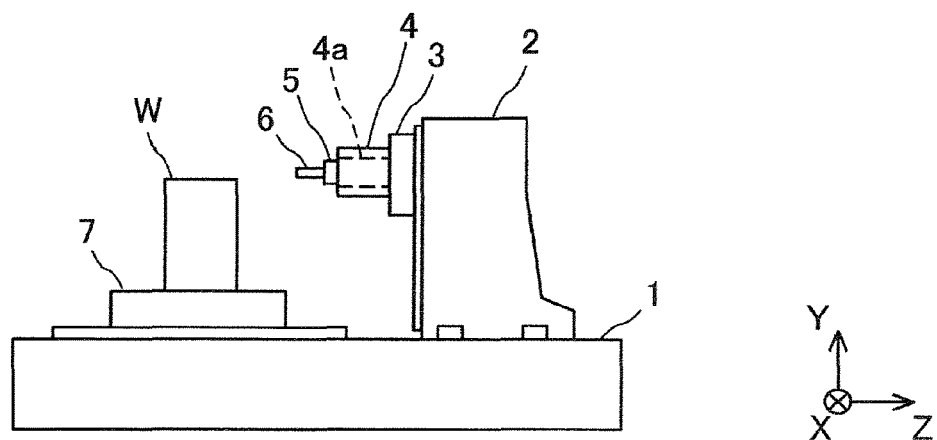
FIG. 1 is a constructional diagram showing a machine tool in first embodiment according to the present invention.

One example of the applicable machine tool for the present invention is a horizontal machining center referred to FIG. 1. While the example is the horizontal machining center as the machine tool, however it may be another machining center or another machine tool having a rotational tool.

The machine tool includes three linear axes of an X-axis, a Y-axis and a Z-axis which are orthogonal each other as a driving axis. As shown in FIG. 1, the machine tool includes a bed 1, a column 2 movable along the X-axis on the bed 1, a saddle 3 movable along the Y-axis on a front surface of the column 2, a spindle device 4 mounted on the saddle 3 and having a rotatable spindle 4a, a rotational tool 6 mounted through a tool holder 5 in an end side of the spindle 4a, and a table 7 movable along the Z-axis on the bed 1 and mounting a workpiece W. The machine tool equips an un-illustrated controller controlling each of driving axes.

"Status of Rotational Tool in Machining"

Figure 2:
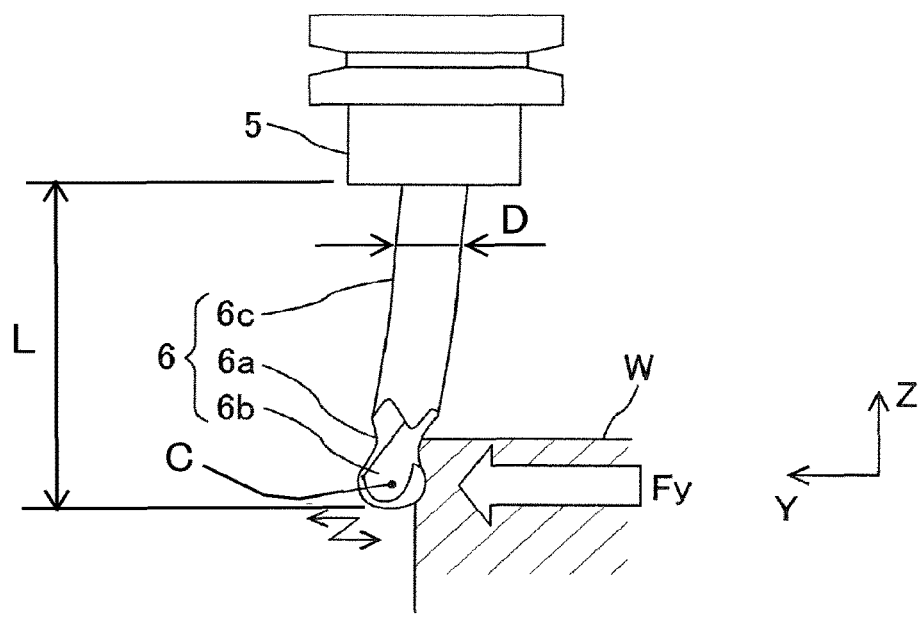
FIG. 2 is a diagram showing a machining status of a rotational tool to a workpiece to show a deflection status of the rotational tool.

It is explained hereinafter the status of the rotational tool 6 during machining the workpiece W by the rotational tool 6. As shown in FIG. 2, the rotational tool 6 includes a plurality of tool tips 6a, 6b on a top end of the rotational tool 6 and a non-tool tip portion 6c on the opposite base portion thereof. A number of tool tips of the rotational tool 6 is two of the tool tips 6a, 6b, however it may be one, three or other number of the tool tips.

Where the tool tips 6a, 6b receive machining resistance Fy from the workpiece W during machining by the rotational tool 6, the tool tips 6a, 6b have a tendency of deflection toward the non-tool tip portion 6c. Especially in a case where an overhang amount L of the tool tips 6a, 6b from the base portion of the non-tool tip portion 6c versus a tool diameter D, that is L/D of the rotational tool 6 is large, it tends to make an amount of deflection of the top end of the rotational tool 6 large by the machining resistance Fy since rigidity of the rotational tool 6 is low because of its narrow and long shape.

If the machining resistance Fy generated in the rotational tool 6 is constant, the amount of the deflection of the top end of the rotational tool 6 is constant. However in fact, the machining resistance Fy is changeable in accordance with an interrupted machining by two of tool tips 6a, 6b of the rotational tool 6 because the machining is not continuous but interrupted by portions without tool tips of the rotational tool 6. As a result, the deformed amount of the deflection of the tool tips 6a, 6b is changeable along a Y-direction as shown by a bi-directional arrow in FIG. 2.

The machining resistance Fy and the deformed amount of the deflection of a rotational center C of the tool tips 6a, 6b of the rotational tool 6 are depended on dynamic characteristic in vibration system in which the tool tips 6a, 6b of the rotational tool 6 are a vibration body of the vibration system. The dynamic characteristic is referred as "dynamic characteristic of the tool tips of the rotational tool" hereinafter. The dynamic characteristic of the tool tips 6a, 6b of the rotational tool 6 shows motion or behavior of the deflection against the force imparted to the tool tips 6a, 6b. The dynamic characteristic is represented with a transfer function or represented with mass coefficient M, natural frequency f, damping ratio calculated from the transfer function, and so on. The transfer function includes mechanical compliance and phase delay. One example of the dynamic characteristic is viscous damping coefficient C and spring coefficient K, and these C and K are calculated from above-identified M, f, $\zeta$.

Next, it will be explained the behavior of the tool tips 6a, 6b of the rotational tool 6 against the machining resistance Fy generated by the rotational tool 6 and against the elapsed time t of the deflection amount Ya of the rotational center C of the tool tips 6a, 6b of the rotational tool 6 in referring to FIG. 3, 4A to 4E where the rotational tool 6 is rotated and fed to machine interruptedly the workpiece W. Here are explained the machining resistance Fy and the deflection amount Ya along a counter cutting direction of the Y direction. The counter cutting direction is explained here because it provides the most effective factor to machining error.

Figure 3:
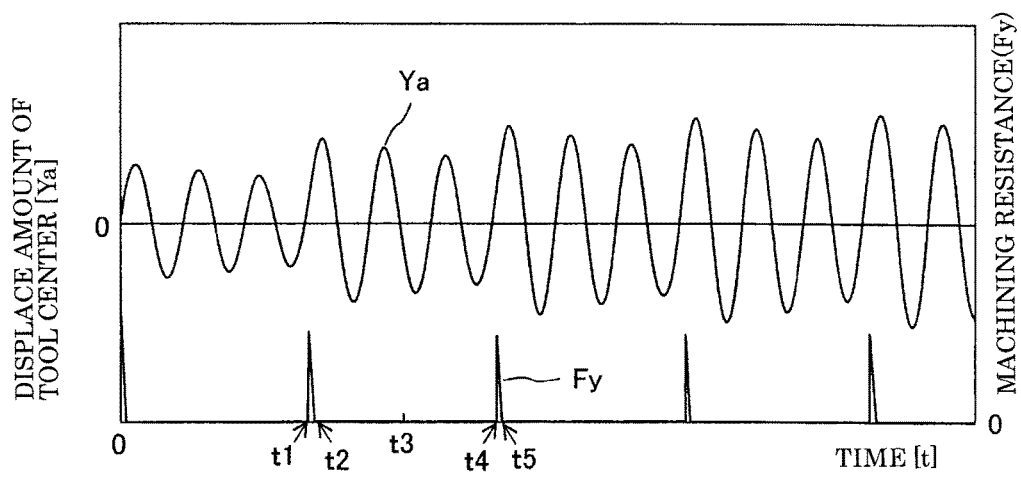
FIG. 3 is a diagram showing both of resistance generated in the rotational tool and a displace amount of a rotational center of the rotational tool to a progressing time.
Figure 4:
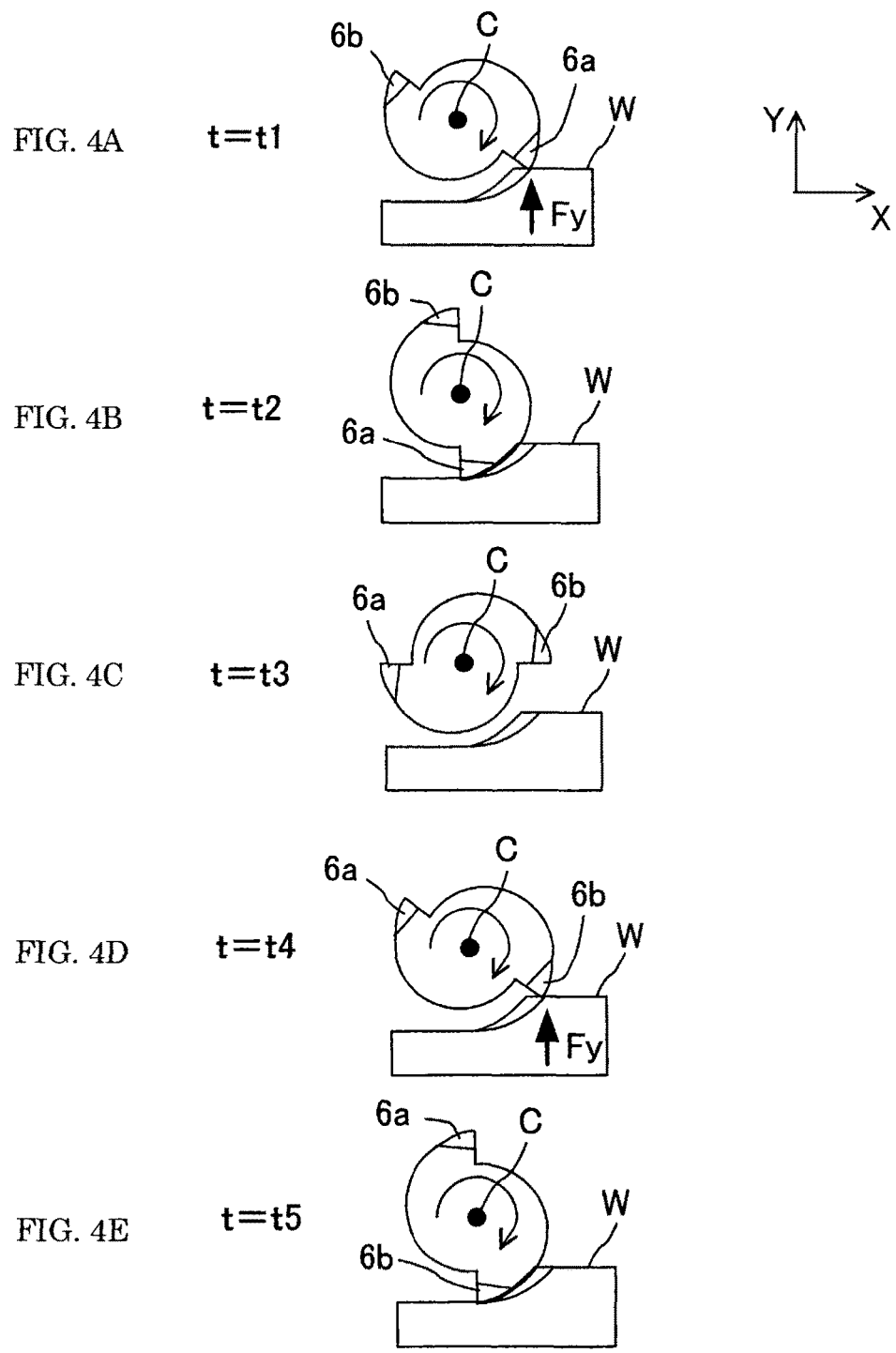
FIG. 4A is a diagram showing a positional relation between the rotational tool and the workpiece at time t1.
FIG. 4B is a diagram showing a positional relation between the rotational tool and the workpiece at time t2.
FIG. 4C is a diagram showing a positional relation between the rotational tool and the workpiece at time t3.
FIG. 4D is a diagram showing a positional relation between the rotational tool and the workpiece at time t4.
FIG. 4E is a diagram showing a positional relation between the rotational tool and the workpiece at time t5.

As shown in FIG. 3, the machining resistance Fy varies to large value at the time t1 from zero and to zero again at the time t2. FIG. 4A and FIG. 4B correspond to the time t1 and t2 respectively in FIG. 3. The time t1 is a time corresponding to the instant one tool tip 6a as shown in FIG. 4A begins to contact with the workpiece W. In other words, the time t1 is the instant time to begin the machining by the tool tip 6a. The time t2 is a time corresponding to the instant that the machining of the workpiece W is finished as shown in FIG. 4B. Therefore, the one tool tip 6a machines the workpiece W between the time t1 and the time t2.

After that, the machining resistance Fy is almost zero between the time t2 and a time t4 as shown in FIG. 3 During this period from the time t2 to the time t3, both tool tips 6a, 6b do not contact with the workpiece W as shown in FIG. 4C corresponding to the time t3. The rotational tool 6 is rotated as an idle rotation to interrupt the machining.

Then, the machining resistance Fy jumps again to the large amount at the time t4 and varies to zero again at a time t5 as shown in FIG. 3. The other tool tip 6b begins to contact with the workpiece W at the time t4 in FIG. 3 as shown in FIG. 4D. It means that the time the machining began by the other tool tip 6b. The machining is finished at the time t5 in FIG. 3 as shown in FIG. 4E corresponding to the time t5. Therefore, the other tool tip 6b machines the workpiece W between the time t4 and the time t5.

It is understood from the machining area shown in FIG. 4A to FIG. 4E that an actual machining amount at each instant time are different between the times t1 and t2 and the times t4 and t5. That is because the actual machining amount is the instant machining amount each machining, and different from a command value of the machining amount. The actual machining amount means the instant machining amount and differs from a commanded value of the machining amount. The actual machining amount jumps to the large amount from the beginning of the machining and reduce gradually after it reaches to a peek. In detail, the actual machining amount varies before and after the boundary between the previously un-machined portion and the previously machined portion. A locus of the machining resistance Fy is almost triangular and is varied in accordance with the actual machining amount as shown in a portion jumped to the large amount of FIG. 3.

As explained above, the machining is performed in interval at times t1 to t2 and t4 to t5, and is not performed in the idle rotation at times t2 to t4. As a result, the rotational tool 6 receives interval force by the interval machining. By this interval force, that is to say the machining resistance generated by the interval machining, the rotational center C of the rotational tool 6 at the top end vibrates along the counter cutting direction of the Y-direction.

FIG. 3 shows a displacement amount Ya of the rotational center C of the tips 6a, 6b of the rotational tool 6 as the vibration according to the natural frequency of the rotational tool 6. Especially, the displacement amount Ya of the rotational center C jumps to the maximum just after the generation of the machining resistance Fy, then damping to repeat to jump and damp.

"Dynamic Characteristic Calculation Apparatus"

The machining resistance Fy and the displacement amount of the rotational center C depend on the dynamic characteristic of the tool tips 6a, 6b of the rotational tool 6. It is therefore important to identify the dynamic characteristic. Next is explained a calculation apparatus for the dynamic characteristic in referring to FIG. 5, FIGS. 6A to 6C and FIG. 7.

Figure 5:
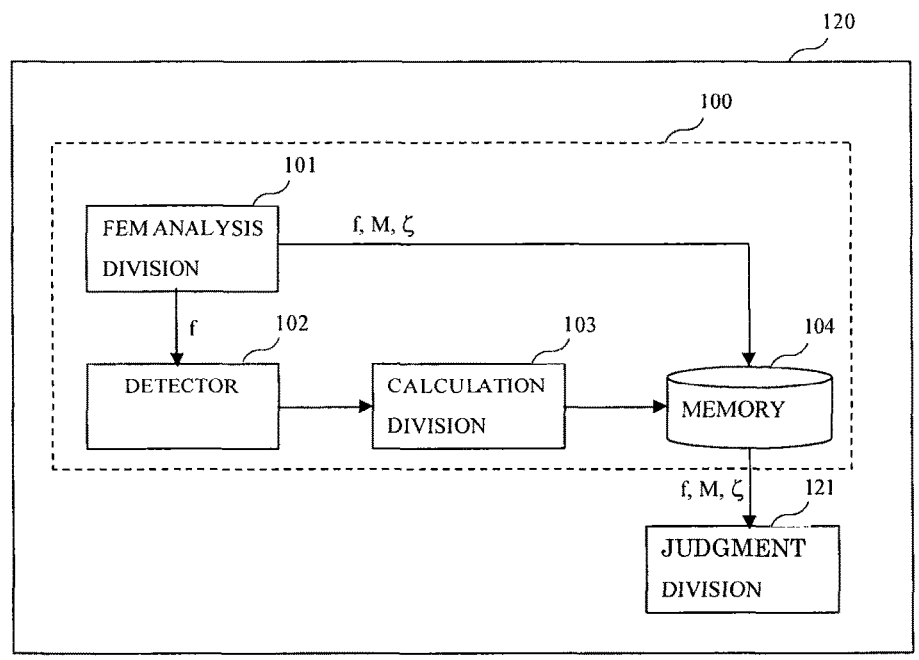
FIG. 5 is a functional block diagram of a machining condition judgment apparatus including the dynamic characteristic calculation apparatus of the machine tool of the first embodiment according to the present invention.

The dynamic characteristic calculation apparatus 100 includes a FEM (Finite Element Method) analysis division 101, a detector 102, a calculation division 103, and a memory 104 as shown in FIG. 5. The FEM analysis division 101 obtains the natural frequency f, the damping ratio $\zeta$ and the mass coefficient M by using the well-known FEM analysis on a basis of constructional information of the machine tool. The dynamic characteristic is easily obtained by the FEM analysis. The constructional information of the machine tool includes information of a form, a material and so on of each of the constructional parts. The FEM analysis division 101 stores in the memory 104 the natural frequency f, the mass coefficient M and the damping ratio to be obtained. The memory 104 receives also the fine natural frequency f calculated by the calculation division 103 in accordance with a result of the detector 102 based on the coarse natural frequency f from the FEM analysis division 101 as explained later.

Wherein, the natural frequency f is represented by next equation (1). Since the damping ratio ζ is small compared to numeral 1 in the equation (1), the value of the equation $\sqrt{1-z^2}$ is nearly equal to one. The damping ratio ζ is represented by next equation (2) and an equation of motion is represented by next equation (3) wherein C is linear viscous damping coefficient, K is spring constant, F is external force, x is amount of displacement, x-dot (ζ) is velocity amount of displacement, and x-two-dot (ζ) is acceleration amount of displacement.

$$f = \frac{\sqrt{1-\zeta^2}}{2\pi} \cdot \sqrt{\frac{K}{M}} \quad (1)$$

$$\zeta = \frac{C}{2\sqrt{K \cdot M}} \quad (2)$$

$$M \cdot \ddot{x} + C \cdot \dot{x} + K \cdot x = F \quad (3)$$

Figure 6A:
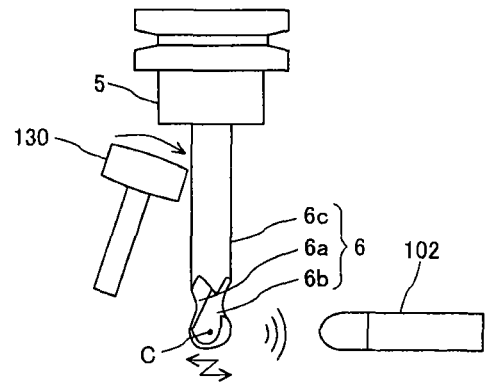
FIG. 6A is a diagram showing first example of exciting the rotational tool to vibrate when a detector shown in FIG. 5 detects the acoustic wave.
Figure 6B:
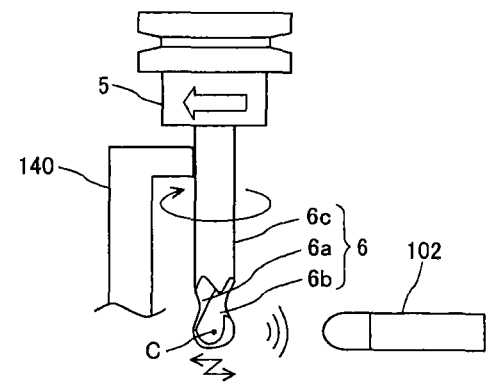
FIG. 6B is a diagram showing second example of exciting the rotational tool to vibrate.
Figure 6C:
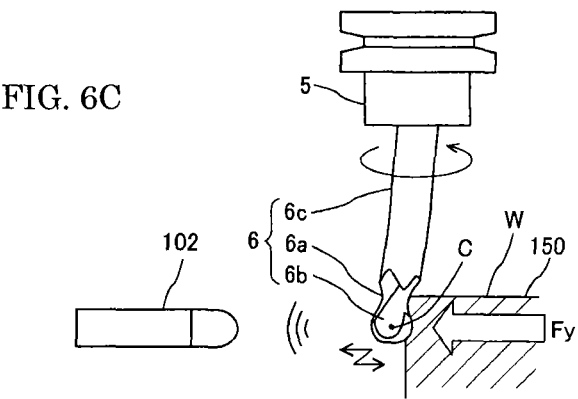
FIG. 6C is a diagram showing third example of exciting the rotational tool to vibrate.

The detector 102 is an acoustic wave detector in this embodiment. It is described hereinafter an application example of the detector 102 in referring to FIGS. 6A to 6C. The detector 102 is positioned adjacent to the tool tips 6a, 6b of the rotational tool 6 as shown in FIGS. 6A to 6C where the detector 102 is positioned without accuracy but in a relatively loose position with respect to the tool tips 6a, 6b. Since the detector 102 can be positioned in a relatively loose position in comparison with a capacitance displacement sensor needing accurate positioning, it may not need any skilled technology and it can reduce installing time.

The detector 102 detects acoustic wave generated by the vibrations of the rotational tool 6 when the rotational tool 6 is excited to vibrate. First example of the excitation of the rotational tool 6 is to hit the non-tool tip portion 6c of the rotational tool 6 with a hammer 130 by an operator as shown in FIG. 6A. This method is easily performed without additional setting of equipments. The hitting amplitude and direction by the operator does not affect largely to detecting accuracy so that the hitting operation is done without any attention. Since the hitting operation is performed to excite the actual rotational tool 6 itself, it generates the high accurate dynamic characteristic. Since the hammer 130 hits not the tips 6a, 6b but the non-tip portion 6c of the rotational tool 6, it can eliminate any influence to the tips 6a, 6b, thereby increasing a life of the tips 6a, 6b.

As second example of exciting to vibrate, a driving device is equipped with the machine tool to drive a target member 140 in order to hit the non-tool tip portion 6c of the rotational tool 6, thereby exciting the vibration of the rotational tool 6 as shown in FIG. 6B. This makes possibility of automatic vibration of the rotational tool 6 during the rotation for hammering without a man power. Since the automatic vibration is performed to hit the actual rotational tool 6 in rotating, it is possible to produce high precision dynamic characteristic. In the case of rotation with same rotational direction in machining, it can produce the dynamic characteristic in nearly equal to the actual machining. Moreover, the non-tool tip portion 6c is hit without being hit the tips 6a, 6b of the rotational tool 6, it can increases the life of the tips 6a, 6b.

Since the hit is done without the man power and is performed just before a real machining, the hit presents the dynamic characteristic just prior to the actual machining. Since an amount of the exciting power to vibrate the rotational tool 6 is set precisely, it is possible to vibrate the rotational tool 6 surely to be detected by the detector 102. While the excitation of the vibration is in the rotation of the rotational tool 6, however it may be excited without the rotation of the rotational tool 6.

As third example of exciting to vibrate, a driving device is equipped with the machine tool to rotate the rotational tool 6 in counter direction of the rotation, and to contact the tool tips 6a, 6b of the rotational tool 6 with the workpiece W as a target member 150, thereby exciting the vibration of the rotational tool 6 as shown in FIG. 6C. In this case the target member 150 is not cut by the rotational tool 6 because the rotational direction is the reversed direction to the rotational direction in machining. While the workpiece W is used as the target member 150, however it may use another target member 150 instead for the workpiece W, thereby reducing consumption of the target member 150.

Figure 7:
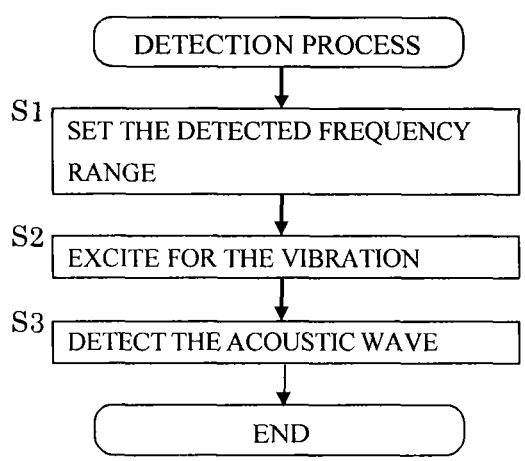
FIG. 7 is a flow chart showing a detection process by the detector shown in FIG. 5.

It is explained hereinafter an acoustic wave detection process by the detector 102 in referring to a flow chart of the FIG. 7. The detector 102 includes a plurality of frequency bands and detects the acoustic wave with certain frequency band being set in a range of the frequency bands. The range of the frequency bands as a detecting condition of the detector 102 is set as a range of the detected frequency bands including the natural frequency f obtained by the FEM analysis division 101 in a step S1. Thereby, the detector 102 can obtain the acoustic wave including the actual natural frequency f certainly and finely.

In a step S2, the rotational tool 6 is excited by one of exciting methods disclosed in FIG. 6A to FIG. 6C. In a step S3, the detector 102 detects the acoustic wave generated by the rotational tool 6 in accordance with the vibration of the rotational tool 6 caused by the exciting.

The calculation division 103 calculates the natural frequency f on a basis of the detected acoustic wave by the detector 102. The natural frequency f can be calculated from the frequency of the detected acoustic wave. The calculation division 103 replaces the natural frequency f registered in the memory 104 by the FEM analysis division 101 to the calculated natural frequency f and registers it in the memory 104. That is to say, the natural frequency f registered in the memory 104 is the natural frequency f calculated by the calculation division 103.

An actual mounting position of the rotational tool 6 on the tool holder 5 becomes slightly different from a designed mounting position in detail by the FEM analysis division 101 because of a possible displacement of positioning by the operator. Therefore, the FEM analysis by the FEM analysis division 101 is not precisely same to the analysis of the actual position of the rotational tool 6 mounted on the tool holder 5. On the other hand, since the acoustic wave detected by the detector 102 is the acoustic wave generated by the actual vibration of the rotational tool 6, the wave is based on the actual position of the rotational tool 6 on the tool holder 5. The natural frequency f obtained by the FEM analysis division 101 is different from the natural frequency f calculated by the calculation division 103. The natural frequency f registered in the memory 104 is the natural frequency f calculated by the calculation division 103, that is to say the actual natural frequency f tips 6a, 6b of the rotational tool 6.

"Relation Between a Rotational Velocity of the Rotational Tool and a Machining Error or a Maximum Amplitude of the Rotational Tool"

Figure 8:
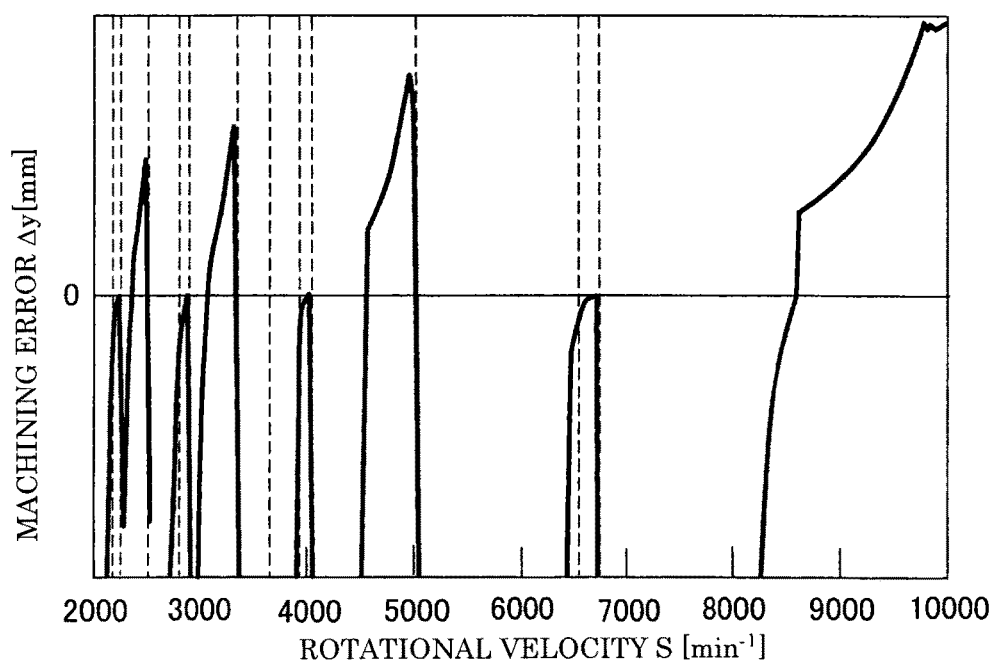
FIG. 8 is a diagram showing machining error to a rotational velocity of the rotational tool.
Figure 9:
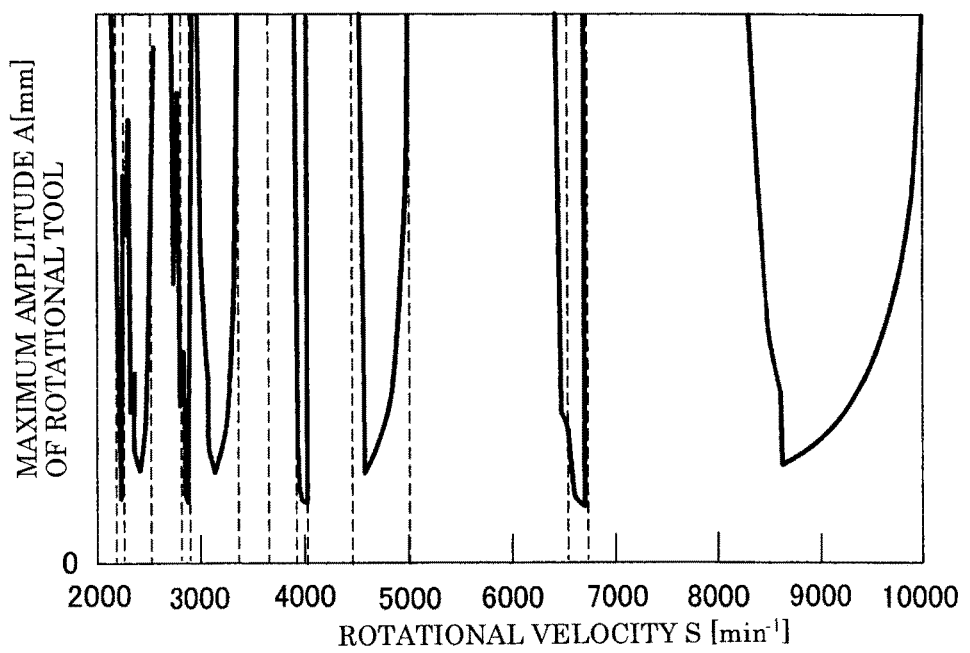
FIG. 9 is a diagram showing maximum amplitude of the rotational tool to the rotational velocity of the rotational tool.

FIG. 8 shows the relation between the rotational velocity S of the rotational tool 6 and the machining error Δy and FIG. 9 shows the relation between the rotational velocity S of the rotational tool 6 and the maximum amplitude A of the rotational tool 6. For example, where the rotational velocity S is around 6,500 $min^{-1}$, it shows the machining error Δy and the maximum amplitude A are small. Therefore, the machining error Δy and the maximum amplitude A are changeable in accordance with changes of the rotational velocity S of the rotational tool 6. This is caused by the change in the relation between the dynamic characteristic in the vibration system of the tips 6a, 6b of the rotational tool 6 and the frequency at the contact of the tips 6a, 6b of the rotational tool 6 with the workpiece W. The dynamic characteristic is not changeable in the vibration system of the rotational tool 6, but the frequency is changeable when the tips 6a, 6b contact with the workpiece W in accordance with the rotational velocity S of the rotational tool 6. As explained above, the machining error Δy and the maximum amplitude A become large or small depending to the relation between the dynamic characteristic and the rotational velocity S of the tips 6a, 6b of the rotational tool 6.

The relationships shown in FIG. 8 and FIG. 9 can be illustrated if the dynamic characteristic of the tips 6a, 6b of the rotational tool 6 are obtained. Where the dynamic characteristics of the tips 6a, 6b of the rotational tool 6 are obtained, the rotational velocity S able to make small machining error Δy and small maximum amplitude A is found. This teaches that to obtain accurate natural frequency is necessary for obtaining the high machining accuracy.

"Application Example of the Dynamic Characteristic Calculation Apparatus"

It is explained hereinafter the application example of the dynamic characteristic calculation apparatus in referring to FIG. 5. The dynamic characteristic calculation apparatus 100 can be functioned as a part of a machining condition judgment apparatus 120 as shown in FIG. 5. A judgment division 121 of the machining condition judgment apparatus 120 introduces the relation between the rotational velocity S and the machining error Δy or the maximum amplitude A as shown in FIG. 8 and FIG. 9 by using the registered dynamic characteristic of the tool tips 6a, 6b of the rotational tool 6 in the memory 104. The judgment division 121 memorizes a range of the rotational velocity S with the machining error Δy or the maximum amplitude A being smaller than a threshold value.

The judgment division 121 judges whether a command value of the rotational velocity S included in a present machining condition is within the registered range of the rotational velocity S. Where the command value is within the registered range, the judgment division 121 judges the present machining condition is fine and the machining is performed by the machining condition. Where the command value is not within the registered range, the judgment division 121 changes the command value of the rotational velocity S.

According to the first embodiment the present invention can obtain the actual natural frequency f because the natural frequency f is calculated on a basis of the acoustic wave generated by vibrating the actual rotational tool 6. Therefore, the machining condition can be decided and the machining condition achieves the desired machining accuracy where the tips 6a, 6b of the rotational tool 6 is bent and vibrated against the base portion of the rotational tool 6.

The mass coefficient M and the damping ratio ζ are obtained by the FEM analysis wherein the influence amount to the machining accuracy by the displacement of the mass coefficient M and the damping ratio ζ is small in comparison to the displacement of the natural frequency f. Therefore, it is easy to obtain the mass coefficient M and the damping ratio ζ by the FEM analysis, thereby to obtain sufficient machining accuracy.

While the invention has been described in detail with reference to the preferred embodiment, it will be apparent to those skilled in the art that the invention is not limited to the present embodiment, and that the invention may be realized in various other embodiments within the scope of the claims.

Second Embodiment

While the mass coefficient M and the damping ratio ζ of the dynamic characteristic of the tips 6a, 6b of the rotational tool 6 are obtained by the FEM analysis, however the present invention is not limited to the construction, but the calculation division 103 may calculate the damping ratio ζ in addition to the natural frequency f by using the acoustic wave generated by the vibration of the rotational tool 6 in the second embodiment of the present invention.

In the second embodiment, the FEM analysis division 101 obtains the mass coefficient M and the damping ratio ζ by the FEM analysis. The calculation division 103 calculates not only the natural frequency f but the damping ratio ζ on a basis of the detected acoustic wave by the detector 102. The calculation division 103 registers the calculated natural frequency f and the calculated damping ratio ζ in the memory 104.

The second embodiment of the present invention can introduce the relation between the rotational velocity S and the machining error Δy or the maximum amplitude A as shown in FIG. 8 and FIG. 9 by obtaining the natural frequency f and the damping ratio ζ in accordance with the actual rotational tool 6. Thereby, the machining condition can be decided and can obtain the desired high machining accuracy.

Other Embodiment

While the detector 102 is the acoustic wave detector, however the present invention is not limited to the construction, but it may be a magnetic sensor detecting the magnetic changeable in accordance with the vibration of the rotational tool 6. The magnetic sensor can be installed without any skilled techniques because of its high freedom of installation, thereby reducing the installing time. This other embodiment has the same effect to that of the first and the second embodiment.

What is claimed is:

1. An apparatus calculating a dynamic characteristic of a machine tool that executes an interrupted machining of a workpiece by moving a rotational tool having one or plural tool tips relative to the workpiece comprising:
   a vibration detector configured to detect a vibration property of said rotational tool mounted on the machine tool when said rotational tool is excited to vibrate by a target member prior to the interrupted machining of the workpiece; and
   a processor configured to:
   calculate a natural frequency of said rotational tool mounted on the machine tool on a basis of said detected vibration property, replace a pre-excitation natural frequency stored in a memory with said calculated natural frequency, said pre-excitation frequency being determined based on constructional information of said machine tool before said rotation tool is excited to vibrate by the target member, and generate a command for said machine tool to change a rotational velocity of said rotational tool in said interrupted machining based upon said calculated natural frequency, wherein said machine tool includes a driving device configured to move said rotational tool relative to said workpiece; and said rotational tool is excited to vibrate, prior to the interrupted machining of the workpiece, by contacting said rotational tool with said target member mounted on said machine tool without use of man power by driving said driving device without said rotational tool being rotated, or said rotational tool is excited to vibrate prior to the interrupted machining of the workpiece by contacting said rotational tool with said target member by driving said driving device while said rotational tool is rotated in a counter rotational direction against a rotational direction of the tool when machining.

2. The apparatus according to claim 1, wherein
said rotational tool is mounted on a tool holder fixed on a spindle of said machine tool;
said rotational tool includes said one or plural tool tips at a top side and a non-tip portion at a base side; and
said rotational tool is excited to vibrate prior to the interrupted machining of the workpiece by contacting said non-tip portion of said rotational tool with said target member by driving said driving device.

3. The apparatus according to claim 1, wherein
said dynamic characteristic includes said pre-excitation natural frequency and a mass coefficient of said one or plural tool tips; and
said processor is configured to determine said mass coefficient by executing a Finite Element Method (FEM) analysis based on said constructional information of said machine tool.

4. The apparatus according to claim 3, wherein
said processor is configured to determine said pre-excitation natural frequency by executing said FEM analysis; and
said vibration detector is configured to detect said vibration property when a detecting condition, determined on a basis of said pre-excitation natural frequency, occurs.

5. The apparatus according to claim 4, wherein
said dynamic characteristic includes a damping ratio; and
said processor is configured to calculate said damping ratio on a basis of said detected vibration property.

6. The apparatus according to claim 3, wherein
said dynamic characteristic includes a damping ratio of said one or plural tool tips; and
said processor is configured to determine said damping ratio by executing said FEM analysis.

7. The apparatus according to claim 1, wherein the vibration detector is an acoustic wave detector configured to detect an acoustic wave generated by vibration of said rotational tool when said rotational tool is excited to vibrate.

8. The apparatus according to claim 1, wherein the vibration detector is a magnetic property detector configured to detect a variable magnetic property generated by vibration of said rotational tool when said rotational tool is excited to vibrate.

9. A method calculating a dynamic characteristic of a machine tool that executes an interrupted machining of a workpiece by moving a rotational tool having one or plural tool tips relative to the workpiece comprising steps of:

detecting a vibration property of said rotational tool mounted on the machine tool when said rotational tool is excited to vibrate by a target member prior to the interrupted machining of the workpiece;

calculating a natural frequency of said rotational tool mounted on the machine tool on a basis of said detected vibration property;

replacing a pre-excitation natural frequency stored in a memory with said calculated natural frequency, said pre-excitation frequency being determined based on constructional information of said machine tool before said rotation tool is excited to vibrate by the target member; and generating a command for said machine tool to change a rotational velocity of said rotational tool in said interrupted machining based upon said calculated natural frequency, wherein said rotational tool is excited to vibrate, prior to the interrupted machining of the workpiece, by contacting said rotational tool with said target member mounted on said machine tool without use of man power by driving a driving device without said rotational tool being rotated, or said rotational tool is excited to vibrate prior to the interrupted machining of the workpiece by contacting said rotational tool with said target member while said rotational tool is rotated in a counter rotational direction against a rotational direction of the tool when machining.

10. The method according to claim 9, wherein detecting includes detecting an acoustic wave generated by vibration of said rotational tool when said rotational tool is excited to vibrate.

11. The method according to claim 9, wherein detecting includes detecting a variable magnetic property generated by vibration of said rotational tool when said rotational tool is excited to vibrate.

12. A method of calculating a dynamic characteristic of a machine tool that executes an interrupted machining of a workpiece by moving a rotational tool having one or plural tool tips relative to the workpiece, said dynamic characteristic including a mass coefficient and a natural frequency of said rotational tool mounted on the machine tool, said method comprising steps of obtaining said mass coefficient by executing a Finite Element Method (FEM) analysis based on constructional information of said machine tool;

detecting a vibration property of said rotational tool mounted on the machine tool when said rotational tool is excited to vibrate by a target member prior to the interrupted machining of the workpiece;

calculating said natural frequency on a basis of said detected vibration property;

replacing a pre-excitation natural frequency stored in a memory with said calculated natural frequency, said pre-excitation frequency being determined based on said constructional information of said machine tool before said rotation tool is excited to vibrate by the target member; and generating a command for said machine tool to change a rotational velocity of said rotational tool in said interrupted machining based upon said calculated natural frequency, wherein said rotational tool is excited to vibrate, prior to the interrupted machining of the workpiece, by contacting said rotational tool with said target member mounted on said machine tool without use of man power by driving a driving device without said rotational tool being rotated, or said rotational tool is excited to vibrate prior to the interrupted machining of the workpiece by contacting said rotational tool with said target member while said rotational tool is rotated in a counter rotational direction against a rotational direction of the tool when machining.

13. The method according to claim 12, wherein detecting includes detecting an acoustic wave generated by vibration of said rotational tool when said rotational tool is excited to vibrate.

14. The method according to claim 12, wherein detecting includes detecting a variable magnetic property generated by vibration of said rotational tool when said rotational tool is excited to vibrate.

* * * * *